United States Patent [19]

Frigg

[11] Patent Number: 5,300,074

[45] Date of Patent: * Apr. 5, 1994

[54] TWO-PART ANGLE PLATE

[75] Inventor: Robert Frigg, Davos, Switzerland

[73] Assignee: Synthes (U.S.A.), Paoli, Pa.

[*] Notice: The portion of the term of this patent subsequent to Dec. 18, 2007 has been disclaimed.

[21] Appl. No.: 803,437

[22] Filed: Dec. 6, 1991

[30] Foreign Application Priority Data

Dec. 17, 1990 [CH] Switzerland .................. 989/90

[51] Int. Cl.$^5$ .............................................. A61B 17/56
[52] U.S. Cl. .......................................... 128/67; 606/69;
606/70; 606/71
[58] Field of Search .................... 606/65, 66, 67, 68,
606/69, 70, 71, 62, 72, 63, 64

[56] References Cited

U.S. PATENT DOCUMENTS

| 2,441,765 | 5/1948 | Hopkins | 606/67 |
| 2,627,855 | 2/1953 | Price | 606/67 |
| 2,761,444 | 9/1956 | Luck | 606/67 |
| 2,834,342 | 5/1958 | Yost | 606/67 |
| 2,874,691 | 2/1959 | Mason | 606/67 |
| 3,029,811 | 4/1962 | Yost | 606/67 |
| 3,256,877 | 6/1966 | Haboush | 606/67 |
| 3,486,500 | 12/1969 | Ball | 606/67 |
| 3,530,854 | 9/1970 | Kearney | 606/67 |
| 3,561,437 | 2/1971 | Orlich | 606/67 |
| 4,978,349 | 12/1990 | Frigg | 606/67 |

Primary Examiner—Michael A. Brown
Attorney, Agent, or Firm—Davis Hoxie Faithfull & Hapgood

[57] ABSTRACT

A device for the setting of bone fractures near joints, particularly in the area of proximal and distal femur fractures, as well as the proximal tibia, has a plate blade (2) designed for implantation in the bone fragment (1) near the joint, and a side plate (4) designed for attachment to the shaft of the tubular bone (3) remote from the joint, which are separably connected.

13 Claims, 9 Drawing Sheets

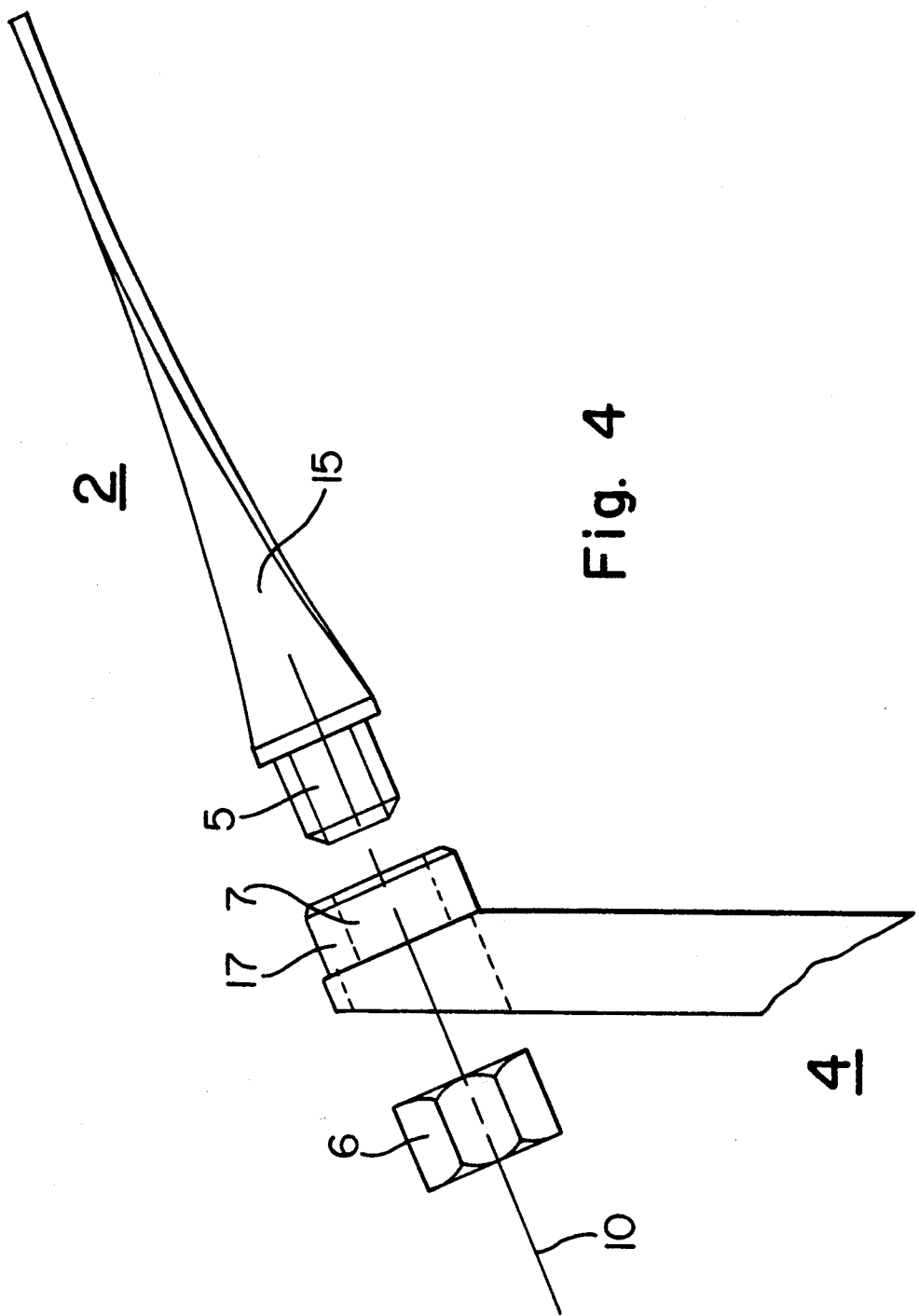

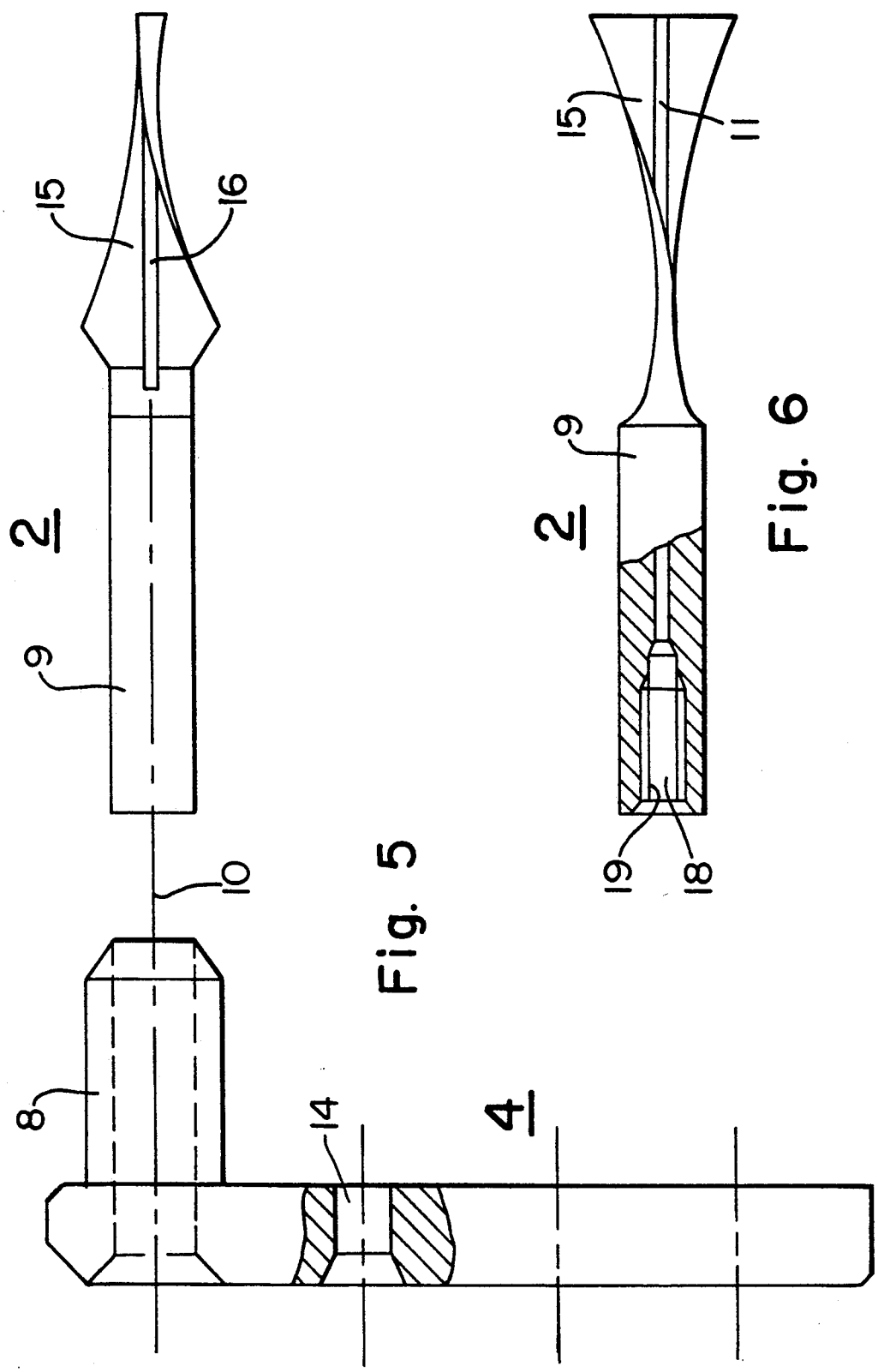

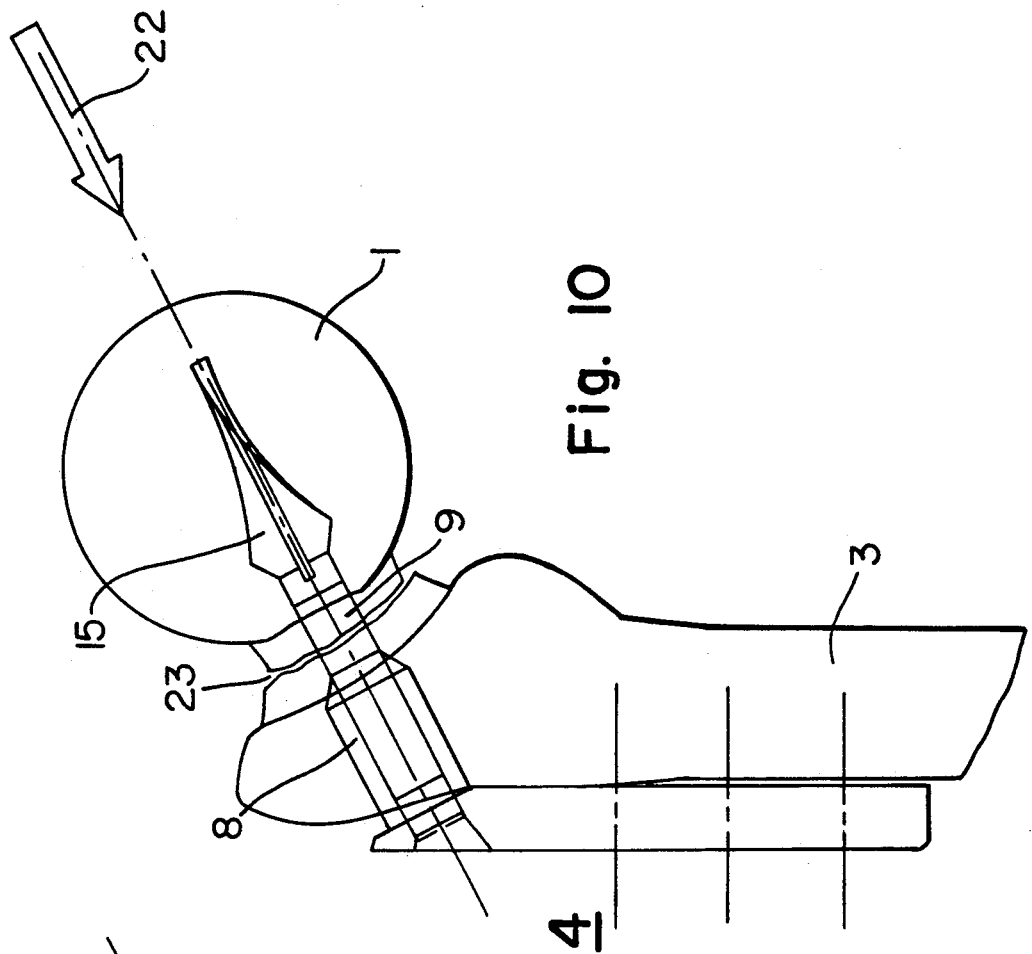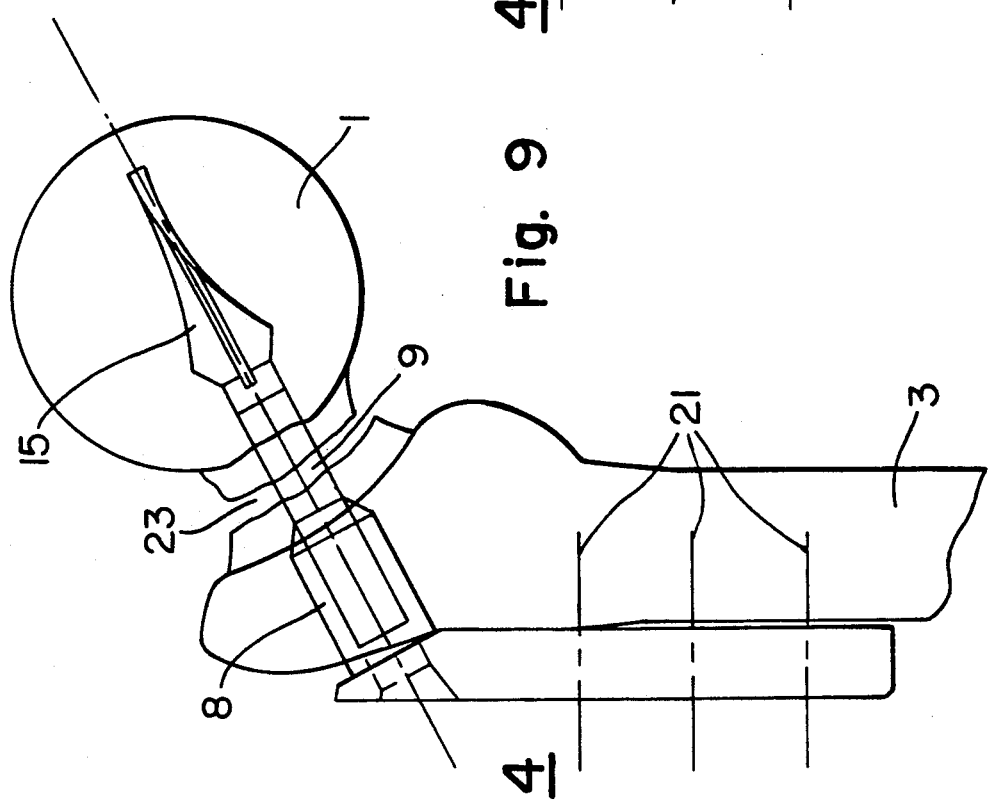

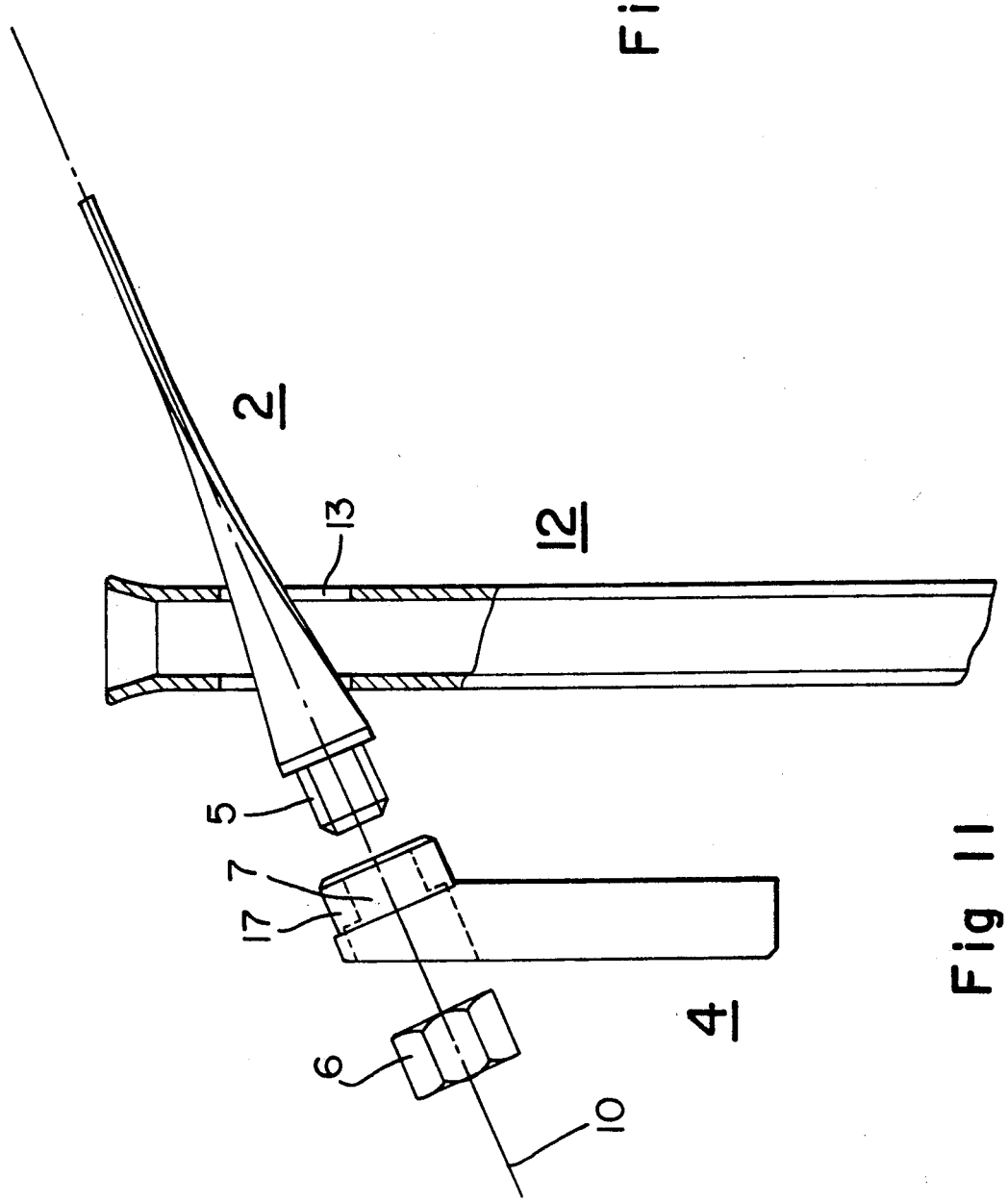

TWO-PART ANGLE PLATE

FIELD OF THE INVENTION

The invention relates to a device for setting bone fractures near joints and in particular to devices for the treatment of fractures in the proximal and distal regions of the femur and in the proximal region of the tibia.

Devices for this purpose, which are commonly known as angle plates, are implanted principally in the treatment of proximal and distal femur fracture, and in fractures of the proximal tibia.

BACKGROUND OF THE INVENTION

As noted, angle plates are currently used in the treatment of joint fractures. See U.S. Pat. No. 3,025,853 to MASON. Typically, an angle plate consists of a plate blade to be guided into the neck of the femur, which blade is permanently connected at a predetermined angle to a side plate to be attached to the femur shaft. The plate blade is driven into the bone at a predetermined angle, and the bone fragment near the joint is thereby gripped. After the plate blade has been completely driven into the neck of the femur, the side plate comes to rest laterally on the proximal femur shaft, where it is attached with a varying number of bone screws.

The advantages that can be achieved with this known angle plate are chiefly of a biomechanical type. Thanks to the broad support area, the blade permits optimum support in the cancellous area of the bone fragment near the joint.

The principal disadvantages of a conventional angle plate relate to its handling. Because of its single-unit construction, a great deal of attention must be paid to the orientation of the blade, as otherwise the longitudinal axis of the side plate will not accord with the longitudinal axis of the tubular bone. Another marginal condition is created by the anatomy of the bone to be set. The direction in which the plate blade is driven in, for example at the proximal femur head, from lateral to medial, must not cause the blade to break out sideways (toward the anterior or posterior) through the femur neck. If the three angular relations are defined by the surgeon, the exact point of entry of the plate blade must be determined. This point of entry is theoretically determined from the three aforesaid angle relations. In practice, there are often deliberate or accidental divergences. Accidental divergences are extremely difficult, if not impossible, to correct because they become visible only after the implantation of the plate blade has been completed. Since the dimension of the plate blade takes up almost the entire section of the femur neck when the plate blade is applied to the proximal femur (the most frequent application), a correction is possible to only a limited extent, and it leads to an unstable setting through the seat of the plate blade, which is now too large.

The implanting of such known angle plates thus requires an outstanding three-dimensional visualization ability on the part of the surgeon in the domain of anatomy, as well as careful, and thus time-consuming, pre-operative planning.

Because of the difficulties that arise with known angle plates, many surgeons have changed to hip screws or condylar screws. With respect to handling during implantation, these screws offer major advantages, compared to the angle plate. One of the greatest advantages is the possibility of a "pre-exploration" of the screw position with the help of a guide wire. This guide wire is introduced, under x-ray monitoring, into the bone fragment to be set.

Since even these hip screws are driven into the sleeve of the side plate at a fixed angle, here again very precise work is required, via the use of a tracking device and a guide wire; as soon as the guide wire is in the best position in the bone, the hole for the hip screw is drilled over the positioned guide wire. After the hip screw has been driven in, the side plate can be pushed onto the screw shaft. A few known screw types have longitudinal grooves on the screw shaft, which must match with the corresponding lands on the sliding shaft (sleeve) of the side plate; this is not a problem, however, since if the matching is imperfect, the dynamic hip screw can be screwed in again or removed.

The disadvantage of the dynamic hip screw is the often unsatisfactory rotation stability and setting, and the large implant section. When one considers the loads that act on the implant, one recognizes that a hip screw is inferior to the angle plate. The same also applies to the setting of fractures in the area of the femur condylars.

An object of the present invention is to combine the biomechanical advantages of the angle plate with the simple operating technique of the hip screw.

SUMMARY OF THE INVENTION

In accordance with the invention, the foregoing object is obtained by means of a device for setting bones in a region where a tubular bone terminates at a joint which comprises a flat blade for implantation in the region of the joint and a separate side plate for attachment to the shaft of the tubular bone remote from the joint.

BRIEF DESCRIPTION OF THE DRAWINGS

The invention will be further described with reference to the accompanying drawings in which:

FIG. 4 is a view in side elevation of a device according to the invention, in which the plate is permanently connected, at an obtuse angle, with the side plate;

FIG. 5 is a view in side elevation and partly in vertical section, of a device according to the invention, in which the plate blade can be connected telescopically, at a right angle, to the side plate;

FIG. 6 is a view partly in side elevation and partly in vertical section, of the plate blade according to FIG. 5;

FIG. 9 is a schematic view partly in elevation and partly in vertical section of the device according to FIG. 8, implanted in the proximal region of a femur;

FIG. 10 is a schematic view, partly in side elevation and partly in vertical section, of the device according to FIG. 8, implanted in the proximal region of a femur;

FIG. 11 is a view partly in side elevation and partly in vertical section of the device according to FIG. 4, combined with a marrow stud or intramedullary nail having a slot;

FIG. 12 is a partial view in side elevation of the marrow stud of FIG. 11;

FIG. 16 is a schematic view of the head of femur in which has been inserted an intramedullary nail and a blade plate/side plate device according to the invention in which the angle of the blade plate relative to the side plate can be changed.

FIG. 17 is an end view of the device of FIG. 16 showing the side plate in more detail.

FIGS. 18 and 19 show the device of FIG. 16 arranged with two different angles between the blade plate and the side plate.

DETAILED DESCRIPTION OF THE INVENTION

Figure 1:
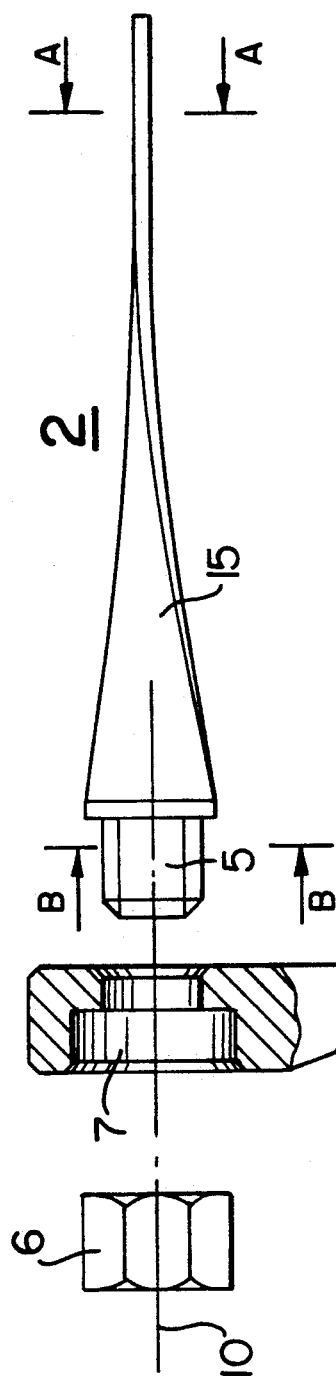
FIG. 1 is an exploded view in side elevation and partly in vertical section of a device according to the invention, in which the plate blade is permanently connected at a right angle to the side plate.
Figure 2:
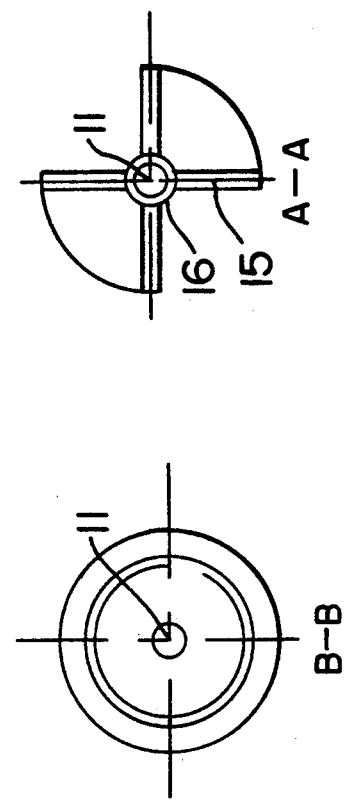
FIG. 2 is a view at section A—A of FIG. 1, showing the twisted configuration of the blade plate.
Figure 3:
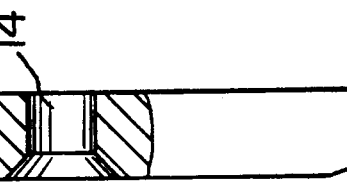
FIG. 3 is a view at section B—B of FIG. 1 of the blade plate.

According to FIGS. 1-3, the device according to the invention consists essentially of a side plate 4 and a plate blade 2 attached to the side plate in such manner that it can be removed. Plate blade 2 has an apical, cylindrical threaded hub 5, which can be inserted into a corresponding socket 7 in the upper portion of the side plate 4. A nut 6 is provided for removably attaching the hub 5 in the socket. To keep the device compact, socket 7 in side plate 4 is designed so that the nut 6 can be countersunk therein.

In the variant of FIG. 1, plate blade 2 has a screw or helically-shaped blade 15, wound around its longitudinal axis 10, preferably in continuous manner, covering an angle of rotation of close to 90°.

Plate blade 2 has a center cannulation 11 running in the direction of its longitudinal axis 10. Cannulation 11 enables the surgeon to position the plate blade 2 over a guide wire, as is done with conventional hip screws. As shown in FIG. 2, plate blade 2 has a thickened section 16 around the cannulation 11, to carry the wing-shaped blades 15 of the plate. The blades 15 can extend over the entire length of the plate blade 2, or over only a portion of it. Depending on the application, instead of the spiral-shaped geometry of the plate blade 2, a flat configuration (not shown) can be used.

FIG. 4 shows a variant of the embodiment according to FIGS. 1-3, in which the plate blade 2 is at an anatomically determined, obtuse angle to the side plate 4, instead of at a right angle. In this embodiment the side plate 4 has a receptacle 17, which through any conventional expedient such as hinge 17a; can swivel within a certain angular range of, say 90° to 150°, can be fixed arbitrarily, as through screw 17b, and contains hole 7. The construction details of this receptacle 17 are not shown in the drawing. In place of hinge 17a, any other conventional construction may be used, such as that shown in U.S. Pat. No. 3,256,877.

Both the embodiment according to FIGS. 1-3 and that of FIG. 4 show a connection between plate blade 2 and side plate 4 that can be disassembled but which is permanent once the implantation has been completed. However, if, as for a hip screw, the indication calls for a sliding connection between plate blade 2 and side plate 4, the lateral end of plate blade 2 can be made as illustrated in FIGS. 5 and 6, in the form of a cylindrical shaft 9 that can be inserted into a corresponding sleeve 8 positioned at the upper end of side plate 4. The cylindrical shaft 9 can be moved telescopically in the sleeve 8. The size of the sleeve 8 must be such that the laterally positioned shaft 9 of the plate blade 2 can slide in it freely.

In this telescoping embodiment, as before, the plate blade 2 is screw-shaped with wings 15 and a center cannulation 11.

As illustrated in FIG. 6, shaft 9 of plate blade 2 can have an axial hole 18 with internal thread 19, so that it can accept a compression screw (not shown in the drawing).

Figure 7:
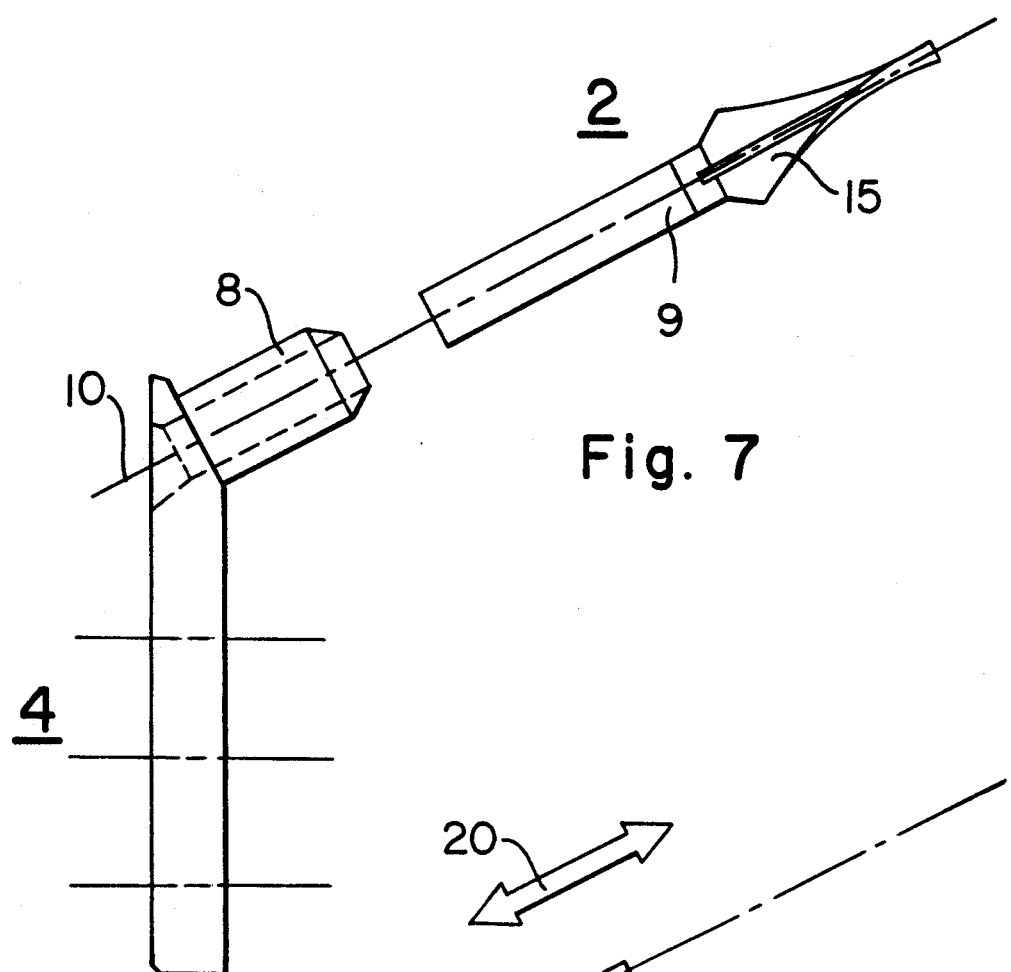
FIG. 7 is a view in side elevation of a device according to the invention, in which the plate blade can be connected telescopically, at an obtuse angle, with the side plate.

FIG. 7 shows another embodiment in which, as in the device of FIG. 4, the plate blade 2 can be connected telescopically, at an obtuse angle, with side plate 4. Here too, sleeve 8 can be housed in side plate 4 preferably in such manner that it can pivot and can be fixed as desired, in various angular positions.

Figure 8:
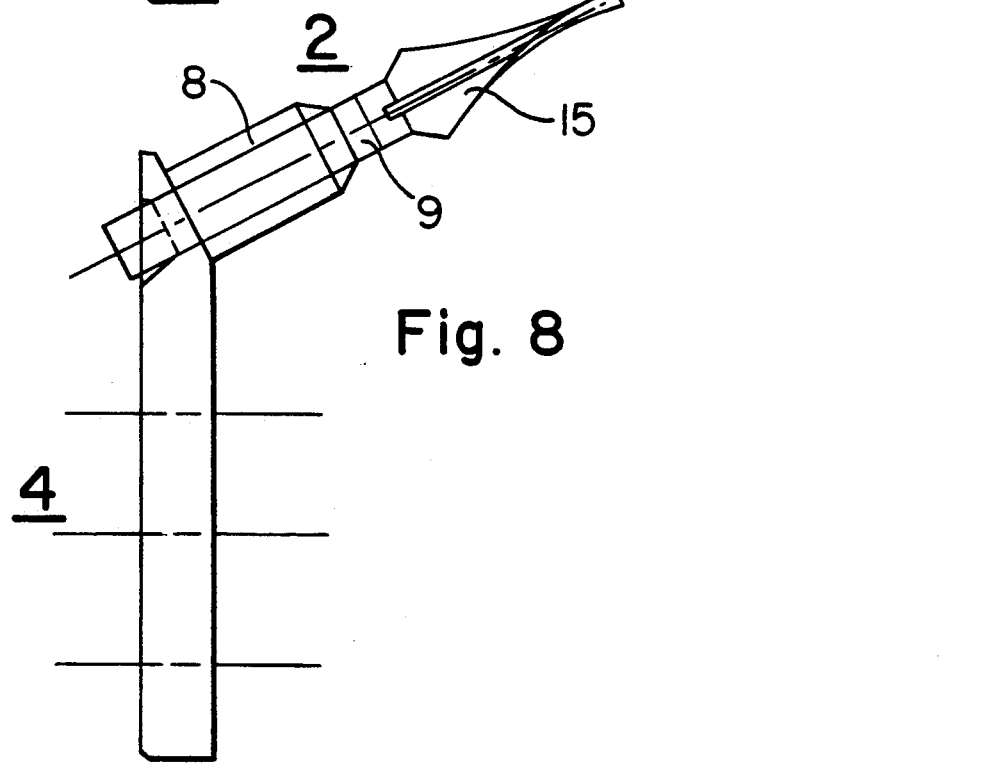
FIG. 8 is a view in side elevation of the assembled device according to FIG. 7, in which the plate blade is housed with its shaft telescopically sliding into the sleeve of the side plate.

FIG. 8 shows the assembled device of FIG. 7, with the shaft 9 of plate blade 2, housed in sliding sleeve 8 of side plate 4 so that it can slide telescopically in the direction of arrow 20.

FIG. 9 shows the still-unloaded device according to FIG. 8, implanted in the proximal region of the femur, for the setting of a fracture of the neck of a femur. The screw-shaped, winding blade 15 of plate blade 2 is implanted in bone fragment 1, the femur head, near the joint. Its shaft 9 is housed telescopically in sleeve 8 of side plate 4, which is attached to tubular bone 3, the femur shaft, away from the joint. The plate may be secured at positions 21 provided therefor. If the joint so fixed is loaded in the direction of arrow 22 (FIG. 10), thanks to the telescopic mobility of plate blade 2, the femur head 1 can move closer to the femur shaft 3 inside sleeve 8, with narrowing of the fracture cleft 23 as shown in FIG. 10. In this embodiment there is thus a dynamic setting of the fracture of the neck of the femur, with the fracture compression being done by the patient's body weight.

Figure 13:
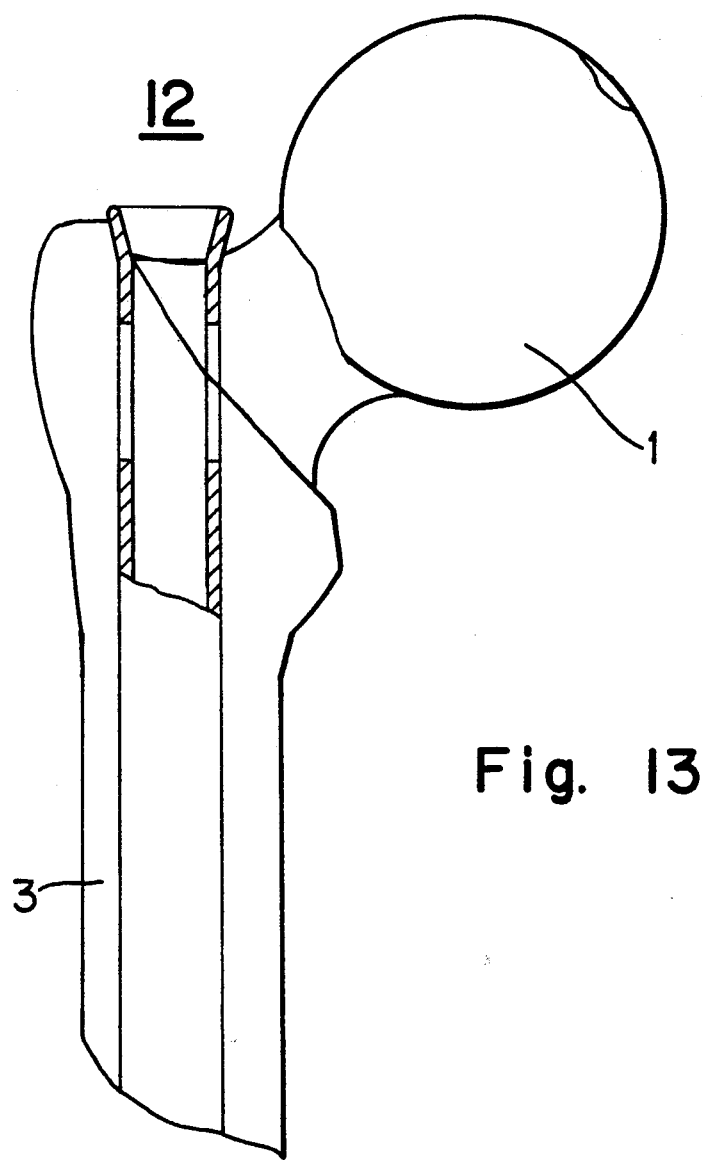
FIG. 13 is a schematic view, partly in side elevation and partly in vertical section of the marrow stud according to FIG. 12, implanted in the proximal region of a femur.

FIGS. 11 and 12 illustrate a device according to the invention as embodied in FIG. 4, combined with a marrow stud 12 having a through slot 13. The implanting of this preferred embodiment is explained below with reference to FIGS. 13-15. As illustrated in FIG. 13, in a first operating step, the marrow stud 13 is implanted in the femur shaft. Slot 13 is turned in the mediolateral direction.

Figure 14:
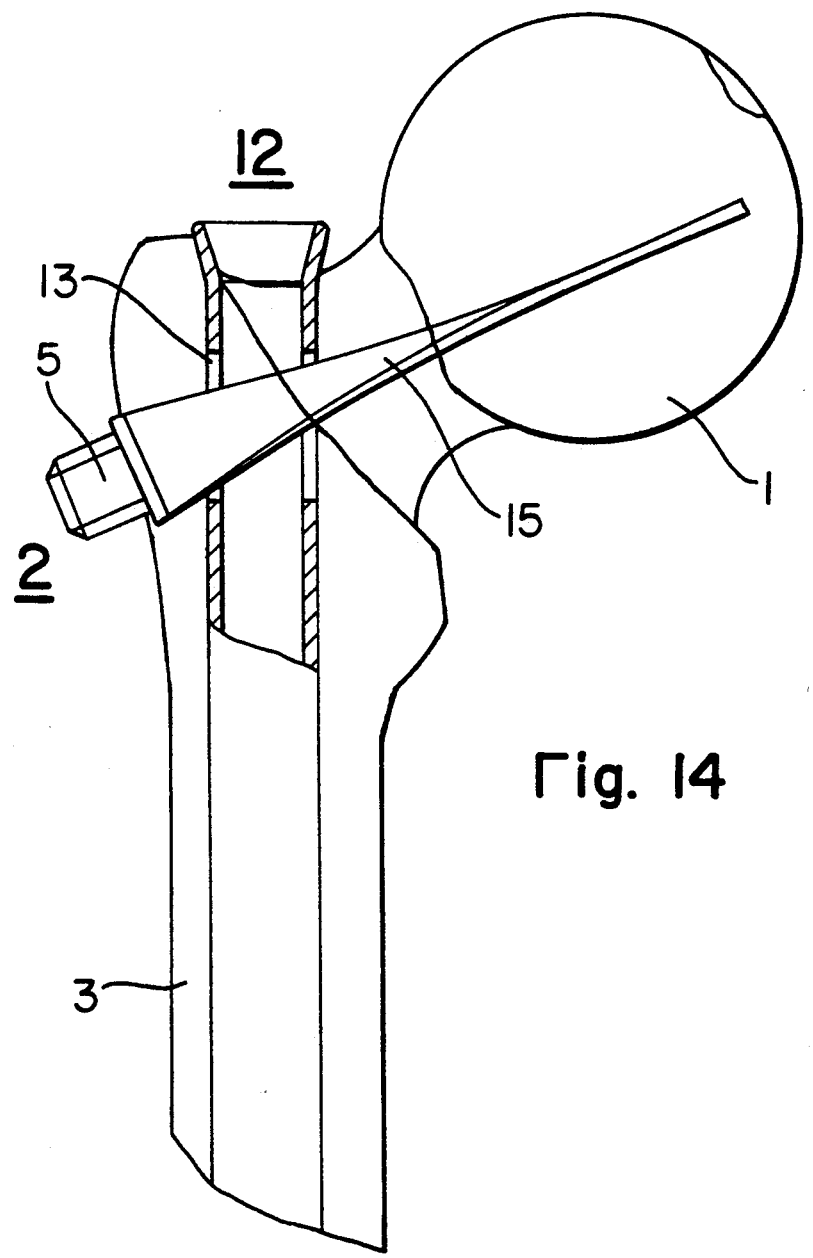
FIG. 14 is a schematic view partly in side elevation and partly in vertical section of the marrow stud of FIG. 12, implanted in the proximal region of a femur, combined with the plate blade with its through slot according to FIG. 11.
Figure 15:
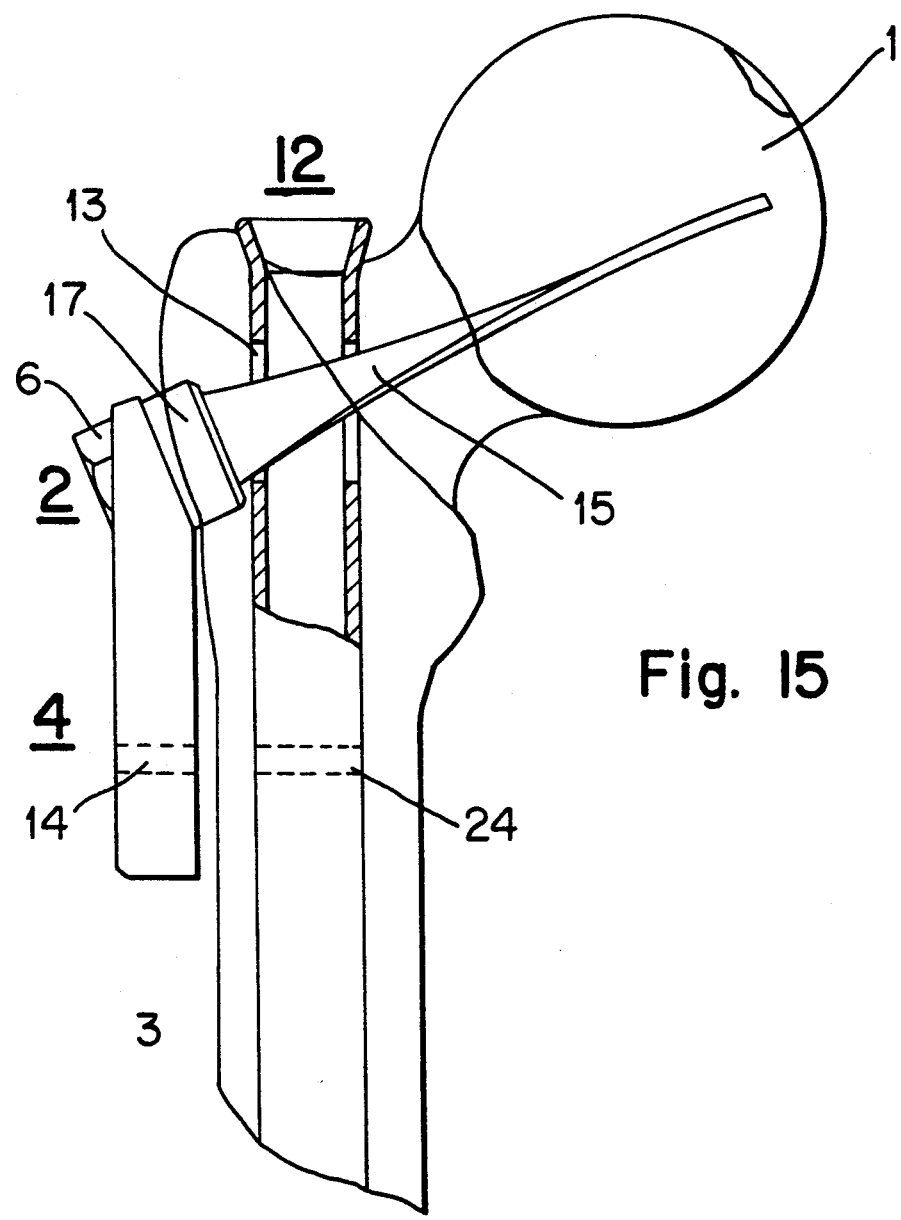
FIG. 15 is a schematic view, partly in side elevation and party in vertical section of a combined blade plate and marrow stud implanted in the proximal region of a femur.

FIG. 14 shows how, in a second step, plate blade 2 with its screw-shaped blade is guided through the slot 13 of marrow stud 12. In a third step shown in FIG. 15, the apical, cylindrical threaded part 5 of plate blade 2 is inserted into the socket in the receptacle 17 in the upper portion of side plate 4, and is fixed therein with a nut 6. Lastly, the side plate 4 is fixed to the femur shaft, in known manner, by means of a number of bone screws (not shown).

Preferably, marrow stud 12 can have holes 24 in its center area, which said holes 24 line up with the holes 14 of the side plate 4. By means of appropriate bone screws, inserted through both holes 14 and 24, side plate 4 can be anchored through the adjacent cortex of femur shaft 3 directly in marrow stud 12, so that an angular or longitudinal positioning of the screw-shaped winding blade 15 is possible with the help of the bone screws inserted through holes 14 and 24.

FIGS. 16 and 17 also illustrate a device 40 according to the invention combined with an intramedullary nail or marrow stud 41. In this case the structure of the device is such as to permit variation in the angle between the blade plate 42 and the side plate 43. As shown more particularly in FIG. 17, side plate 43 has an ovoidal hole 44 to receive an oblong head 45 on blade plate 42. The upper edge 46 of hole 44 rests in a channel 47 formed just inwardly of the head 45 of the blade plate 42 so that the blade plate 42 can be adjusted at various angles relative to side plate 43.

Side plate 43 also includes an elongated slot 48 to receive a screw 49 which is inserted into the shank of the femur and through a hole provided in the nail 41.

As shown in FIGS. 18 and 19, the angle of the blade plate 42 relative to the side plate 43 and the nail 41 can be varied as desired. As indicated above a desirable range is from 90° to 150°.

What is claimed is:

1. A device for setting broken bones in an area where a tubular bone terminates at a joint, comprising a helically twisted plate blade for implantation in a bone fragment near the joint, a separate side plate for attachment to the shaft of the tubular bone remote from the joint, and means for separably connecting the plate blade and the side plate.

2. A device according to claim 1, wherein the plate blade and the side plate are connected by a threaded connection.

3. A device according to claim 2, wherein the threaded connection is positioned relative to the side plate in such manner that it can pivot and be fixed at an angle to the plate.

4. A device according to claim 1, wherein the plate blade and the side plate are connected at an adjustable angle to each other.

5. A device according to claim 4, wherein the side plate has a sleeve and the plate blade has a shaft which can be positioned telescopically in the sleeve.

6. A device according to claim 5 wherein the sleeve is positioned relative to the side plate in such a manner that it can pivot and be fixed at an angle to the plate.

7. A device according to claims 3 or 6, wherein plate blade and side plate can be connected at an angle between said 90° and 150°.

8. A device according to claim 1 wherein the plate blade has a cannulation running in the direction of its longitudinal axis.

9. A device according to claim 1, wherein the side plate has at least one hole to accept a bone screw with which the side plate can be fixed to the shaft of the tubular bone.

10. A device according to claim 9, wherein the marrow stud has a hole for alignment with a hole in the side plate, to receive a bone screw that penetrates both holes.

11. A device according to claim 9, wherein the blade is twisted so that the portion of it lying in the slot of the marrow stud has its largest dimension essentially parallel to the longitudinal axis of the marrow stud and the area lying at the free end of the blade has its largest extension essentially transverse to the longitudinal axis of the marrow stud.

12. A device according to claim 1 and comprising a marrow stud having a through slot for receiving the plate blade.

13. The device according to claim 1, wherein the plate blade has the form of a helix displaced angularly for about 90° from its proximal to its distal end.

* * * * *